United States Patent [19]

Ogura et al.

[11] Patent Number: 4,636,474
[45] Date of Patent: Jan. 13, 1987

[54] TOILET APPARATUS

[75] Inventors: Kenji Ogura, Chigasaki; Takeshi Yamazaki, Tokyo, both of Japan

[73] Assignee: Toto Ltd., Fukuoka, Japan

[21] Appl. No.: 573,315

[22] Filed: Jan. 24, 1984

[30] Foreign Application Priority Data

| Jan. 25, 1983 | [JP] | Japan | 58-11032 |
| Jan. 25, 1983 | [JP] | Japan | 58-11033 |
| Oct. 14, 1983 | [JP] | Japan | 58-192694 |
| Nov. 30, 1983 | [JP] | Japan | 58-225854 |

[51] Int. Cl.⁴ ............................................. C12M 1/34
[52] U.S. Cl. ...................................... 435/291; 4/314; 4/661; 128/638; 435/288
[58] Field of Search ........................... 4/314, 420, 661; 128/630, 638, 749, 760, 761, 771; 422/68, 79; 435/291, 807, 808, 817, 288

[56] References Cited

U.S. PATENT DOCUMENTS

| 3,918,433 | 11/1975 | Fuisz | 128/760 |
| 4,315,990 | 2/1982 | Sheets | 435/291 |
| 4,411,030 | 10/1983 | Kawai et al. | 4/443 |
| 4,466,445 | 8/1984 | Abrams | 128/736 |
| 4,554,687 | 11/1985 | Carter et al. | 4/144.2 |

Primary Examiner—Larry Jones
Assistant Examiner—Allen J. Flanigan
Attorney, Agent, or Firm—Sandler & Greenblum

[57] ABSTRACT

A toilet apparatus is provided in a lavatory having at least one stool, urinal, bidet, or similar toilet structure. The toilet apparatus comprises a detecting sensor for detecting constituents in the feces, urine, or both of a user, and an indicator for indicating or informing the user of his health based upon abnormalities in the constituents detected by the sensor. The apparatus is particularly useful in informing the user of a toilet of his health each time he uses the toilet.

32 Claims, 10 Drawing Figures

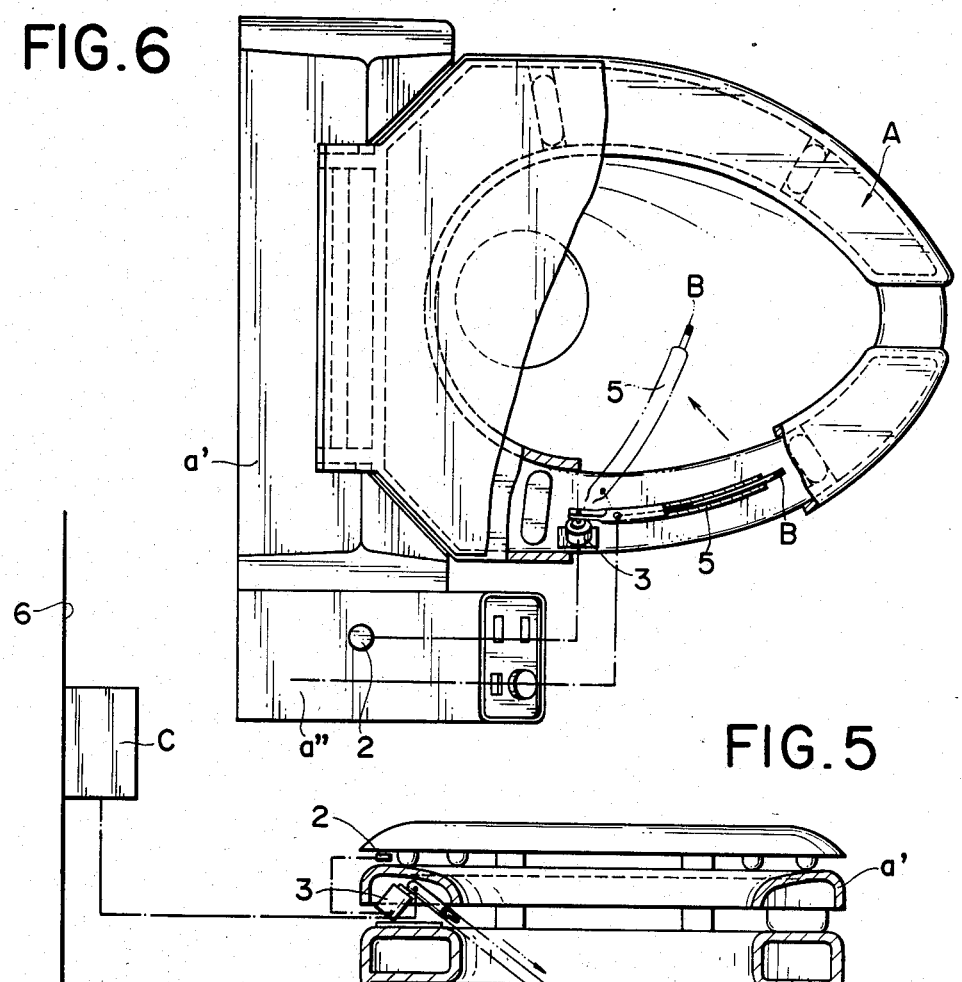
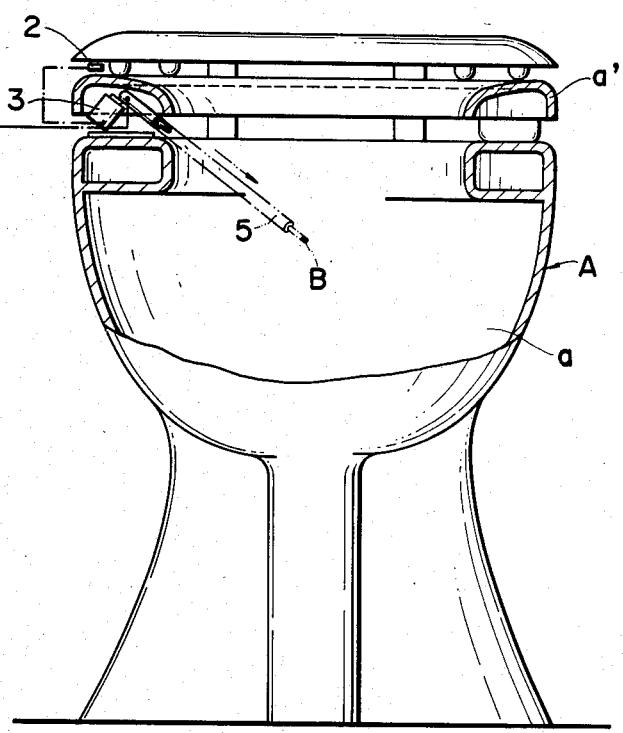

TOILET APPARATUS

BACKGROUND OF THE INVENTION

1. Field of the Invention

The present invention relates to a toilet apparatus provided in a toilet room or laboratory which is provided with at least one stool, urinal, bidet, or similar sanitary facility. More particularly, the invention relates to an apparatus for indicating or displaying the health of a user based upon the urine or feces which has been excreted in the toilet.

2. Discussion of Prior Art

It has long been necessary for users of toilet facilities to check the condition of their health based upon the exrements deposited by them in a toilet. Under such circumstances, normal toilet facility users must contact such excrements via a special test paper, thereafter comparing the change in color of the test paper with a color test chart attached to the wall of a toilet room or similar lavatory facility. There has previously been no other way than manually examining such excrements to ascertain the health of the user. Such circumstances consequently result in unsanitary direct contact between the fingers of a user and his feces or urine. Furthermore, such manual work is itself troublesome, and the results obtained from such inspection may be unsuitable.

SUMMARY OF THE INVENTION

It is a primary object of the invention to provide an improved toilet apparatus which allows the user of a toilet facility to check on his health without physically contacting his feces or urine.

Another object of the invention is to provide a toilet apparatus which will automatically indicate the health of a user based upon an analysis of his own excrements.

These objects are accomplished by a toilet apparatus in accordance with the invention which includes a detecting sensor for detecting constituents of feces, urine, or both, together with an indicator which is electrically connected to the sensor and which is adapted to indicate the health of a user based upon an analysis of the constituents detected by the sensor. The indicator includes a detecting device for detecting the presence of the user on the toilet.

With such an arrangement, a toilet apparatus according to the present invention eliminates the disadvantage of unsanitary physical contact via the finger of the user with his feces or urine.

In order that the present invention can be more clearly understood, preferred embodiments of the invention will be described by way of example with reference to the accompanying drawings.

BRIEF DESCRIPTION OF THE DRAWINGS

FIG. 5 is a front partial sectional view of an apparatus in accordance with the invention in which a sensor is projected inwardly towards a central portion of the toilet bowl by a rotary solenoid which is activated by mechanical switch;

FIG. 6 is a top plan view, taken partially in section, of the toilet apparatus illustrated in FIG. 5;

DETAILED DESCRIPTION OF THE PREFERRED EMBODIMENTS

As illustrated in FIGS. 1-6, a toilet apparatus formed in accordance with the present invention comprises a detecting sensor B and an indicator C. This apparatus is positioned in a toilet room of a lavatory in which at least one stool, urinal, examination urinal, bidet, or similar device is provided.

Detecting sensor B is a conventional biosensor, e.g., an enzyme sensor, organella sensor, tissue sensor, microorganism sensor, immunity sensor, enzyme thermistor, light emitting immunity sensor, BOD sensor, or an electrochemical sensor. Sensor B is adapted to detect constituents such as protein, glucose, and liver juice pigment, which are contained in excrements such as feces and urine.

Figure 1:
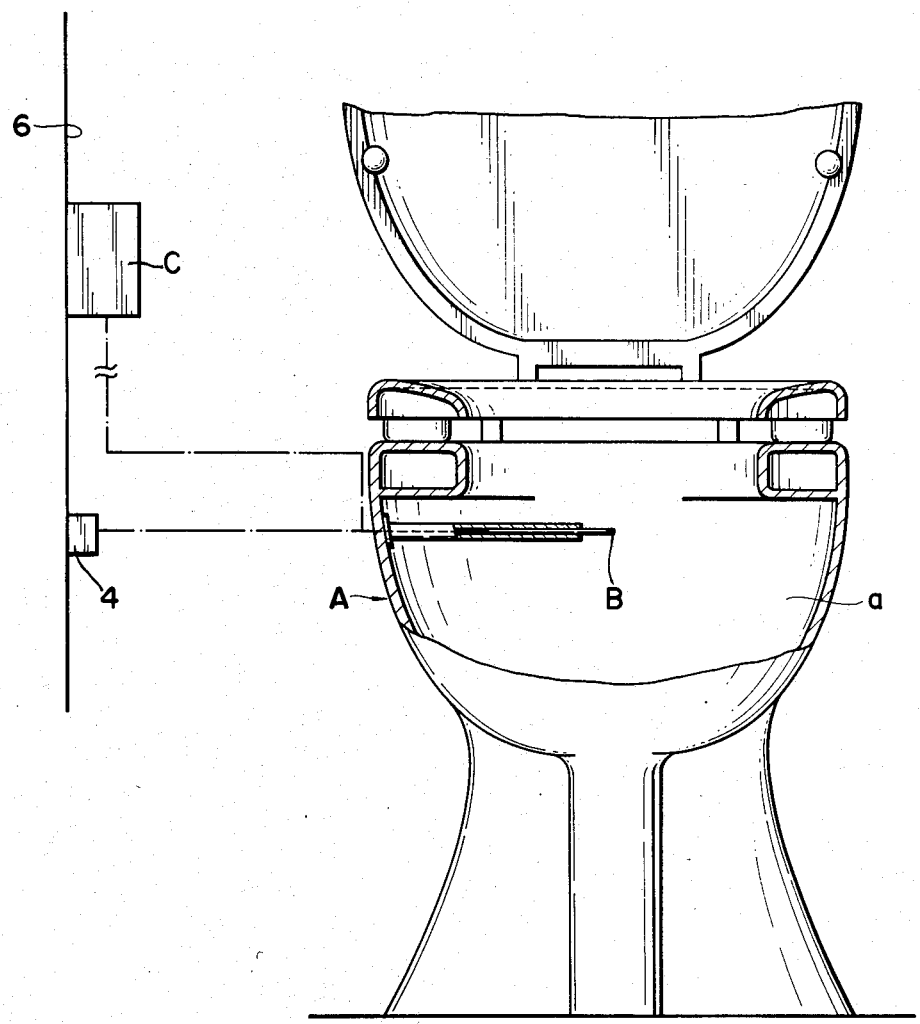
FIG. 1 is a front, partial sectional view of a toilet apparatus in accordance with the present invention in which a sensor and an indicator are continuously activated.
Figure 2:
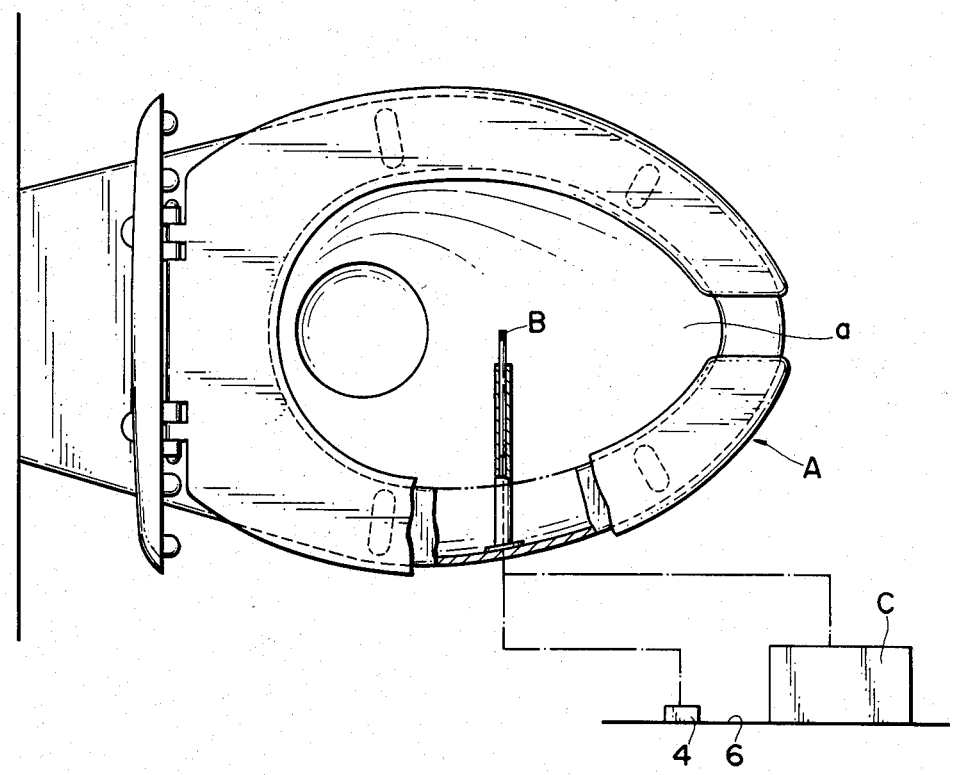
FIG. 2 is a top sectional view, partially in section, of the apparatus illustrated in FIG. 1.
Figure 3:
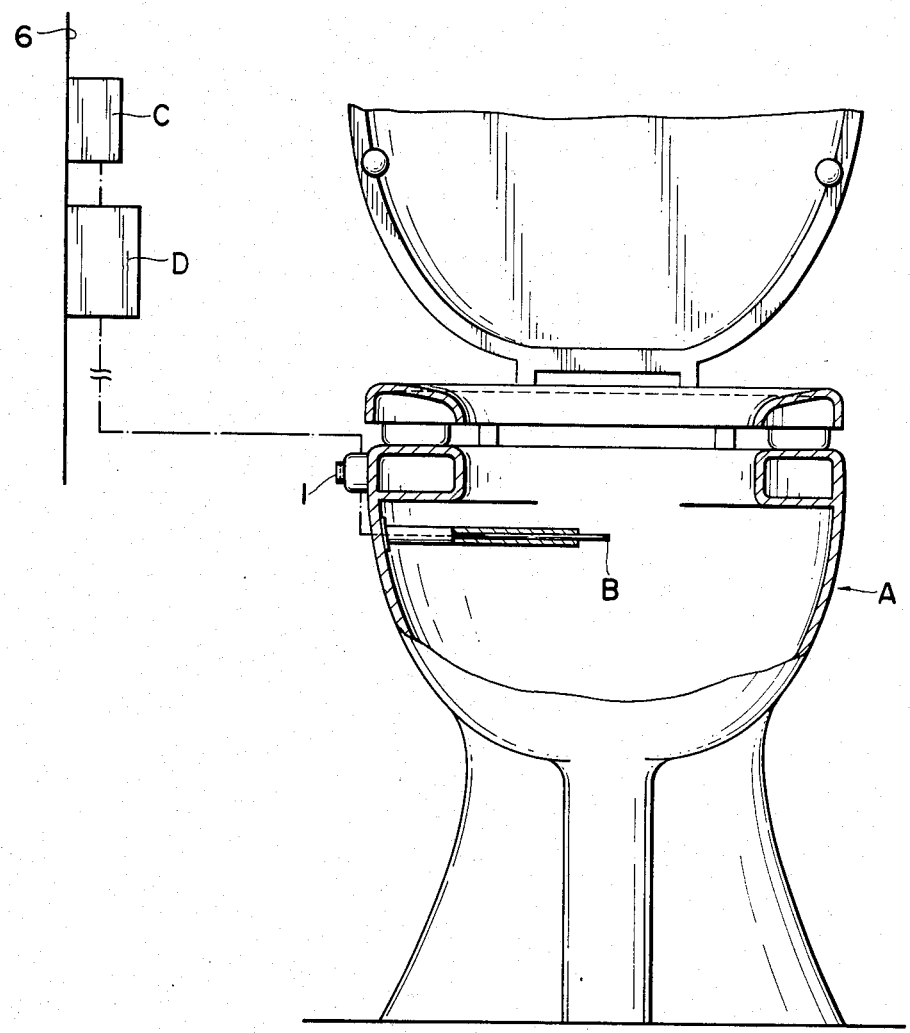
FIG. 3 is a front sectional view of a toilet apparatus in accordance with the present invention in which a detecting sensor is adapted to be manually activated via a push button.
Figure 4:
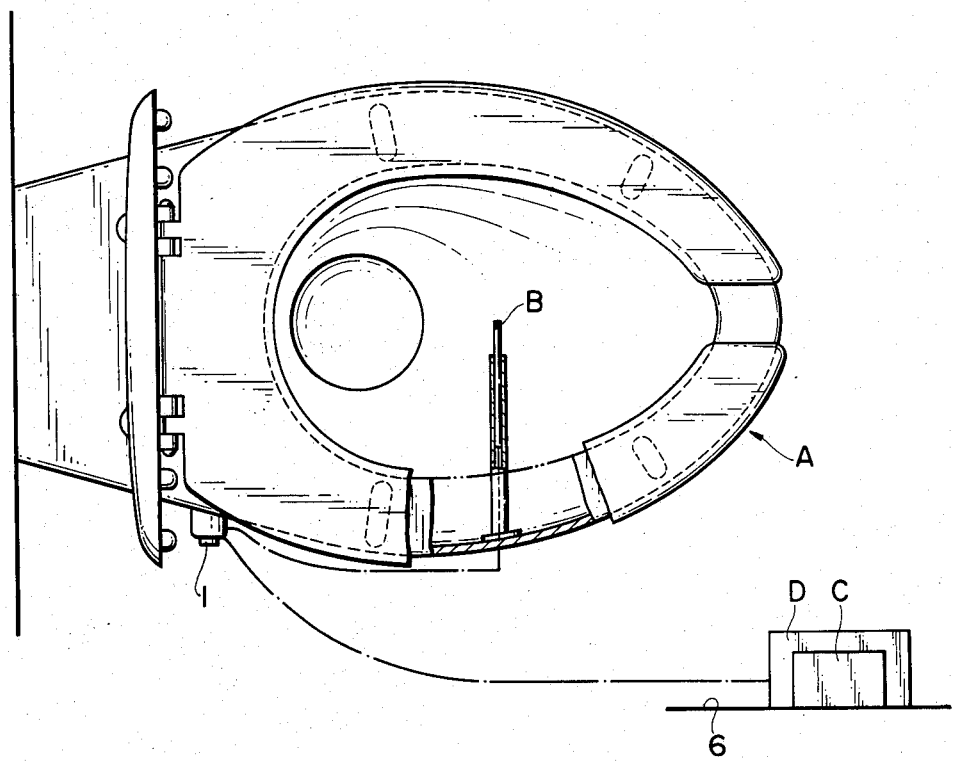
FIG. 4 is a partial top sectional view of the toilet apparatus illustrated in FIG. 3.

Detecting sensor B can be activated in different ways; as illustrated in FIGS. 1 and 2, detecting sensor B can be continuously activated, or as illustrated in FIGS. 3 and 4, it can be selectively activated by manually operating pushbutton 1. Alternately, the sensor can be of the type which is adapted to project into bowl (a) of stool A after it is activated by rotary solenoid 3 when a mechanical switch 2 is pushed, as illustrated in FIGS. 5 and 6.

Detecting sensor B, as illustrated in FIGS. 1 and 2, is in its activated state and is mounted so that it will project directly into bowl (a) in order to directly contact urine or feces, or indirectly contact the urine or feces via water which is retained in bowl (a). When a bidet is used, sensor B is adapted to be fixed directly to the jet nozzle of the bidet. Sensor B is provided to operate in conjunction with indicator C via power source 4.

As illustrated in FIGS. 3 and 4, sensor B can be manually operated by pushing button 1 each time the toilet is used. This occurs via a controller D, which includes a relay and a circuit for connecting the relay to indicator C.

Detecting sensor B, as illustrated in FIGS. 5 and 6, is located below stool seat a', and is provided with a rotary solenoid 3 along arm 5. Solenoid 3 is connected to mechanical switch 2, which is attached to the rear portion of the stool seat or at an upper portion of operation box a".

When the switch is activated, sensor B is pivoted downwardly to move into bowl (a) by movement of rotary solenoid 3, which is also connected to indicator C.

Indicator C comprises a central processing unit, i.e., a CPU, which has prerecorded data equivalent to the values of the urine and/or feces constituents of a healthy person. The indicator is adapted to analyze or evaluate the health of a user based upon the value detected by the sensor, and by an indicating portion which either indicates or displays analyzed data by emitting color, sound, or a blinking lamp. Indicator C is connected to sensor B by a controller D or power source 4, and is provided as a suitable portion of a stool or is attached to toilet room wall 6; in either case it includes a cover portion.

The indicator has a printed circuit which can be arranged so as to indicate whether or not the user of the toilet is healthy, or to blink a lamp or give another indication only when the value of a particular constituent, e.g., protein, is outside of the normal range of values for a healthy person. Other methods of indication can, of course, be devised by one of ordinary skill in the art, depending upon the information which the user wishes to know. Indicator C can optionally be connected to a register or to a memory which will register or record the health of the user. In this way the apparatus of the invention can be used to automatically inform a user of his present health, and as to the possibility of future infirmities.

Figure 7:
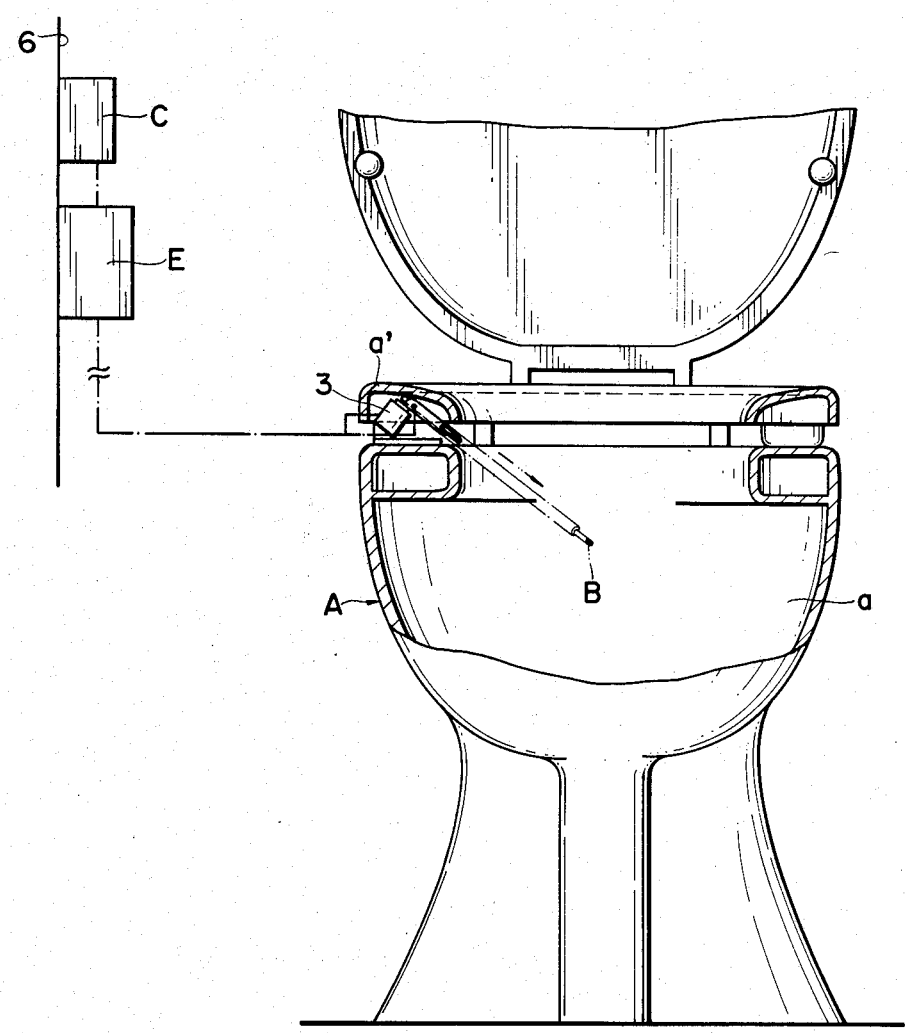
FIG. 7 is a partial sectional view of a toilet apparatus in accordance with the present invention in which a sensor is adapted to be pivoted into the central portion of a toilet bowl when a detecting device detects the presence of a user on the toilet seat.
Figure 8:
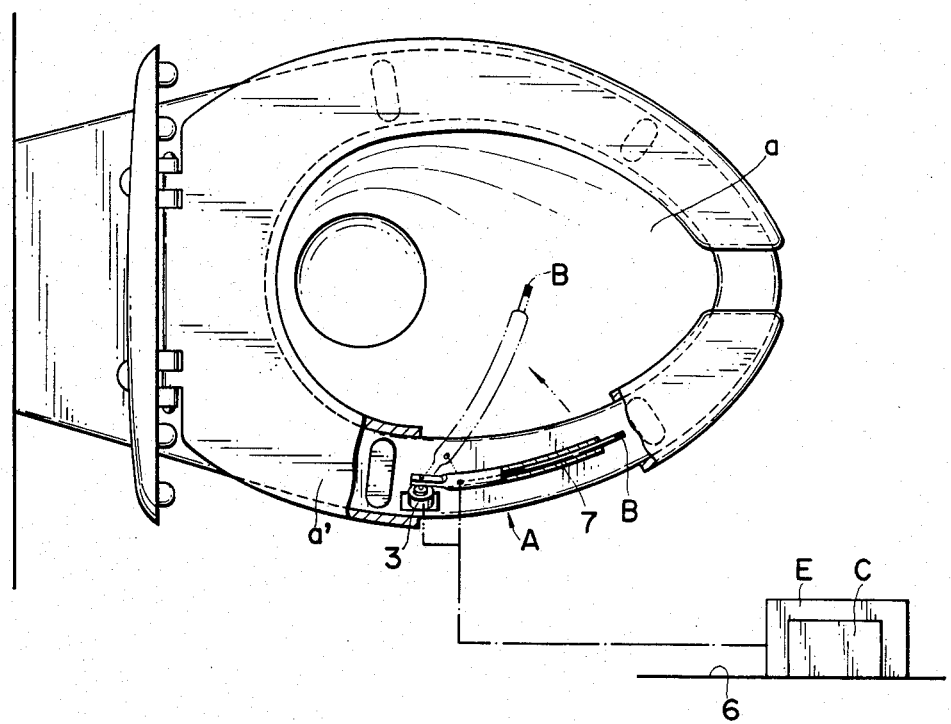
FIG. 8 is a top partial sectional view of the toilet apparatus illustrated in FIG. 7.

FIGS. 7 and 8 illustrate an embodiment of the present apparatus in which a detecting device E is used to detect the presence of a user. This detecting device is connected to both sensor B and indicator C in order to minimize the power required to continuously activate the sensor and indicator, and to eliminate manual operation of the detector.

Detecting device E comprises a receiving circuit having an infrared ray emitting element and an activating or receiving element which receives light radiation reflected from a user. The infrared ray radiation emitting element is activated when the light is received. The detecting device also includes a controller which is electrically connected to the circuit; the circuit and controller are positioned in a covered fashion along a suitable portion of the stool seat or are attached to room wall 6.

The controller comprises an amplifier circuit which is activated by a light receiving circuit, a delay circuit for retarding activation for approximately 3-7 seconds in order to prevent detection of passersby, a connection circuit for activating a rotary solenoid 3 when the delay circuit is released, in order to permit sensor B to be projected via movement of arm 5, the rotary solenoid also serving to activate indicator C. The controller also comprises a strain gauge 7 provided along arm 5 which activates sensor B upon the contact of the arm with feces or urine. The sensor is activated by solenoid 3, which is located below seat body a'.

When the toilet is not being used, detecting sensor B is housed below seat body a', together with rotary solenoid 3; accordingly neither is visible.

The toilet apparatus illustrated in FIGS. 7 and 8 is operated in the following manner: when a user positions himself in front of stool A or a urinal, an infrared ray emitted from the light ray emitting element is reflected by the clothes of a user and is received by the receiving element. The receiving circuit is thus activated and the delay circuit is thereafter activated via the amplifier circuit.

When the delay or retarding circuit is released, sensor B projects into bowl (a) via a rotary solenoid 3. Indicator C then analyzes the constituents which contact Sensor B and will provide the user with an analyzed result.

Sensor B is positioned within seat body a' by the action of a strain gauge 7 which is activated by bending the sensor to contact arm 5 with the excrements of a user. The action of strain gauge 7 is then transmitted to sensor B via a connection circuit and a rotary solenoid 3.

Figure 9:
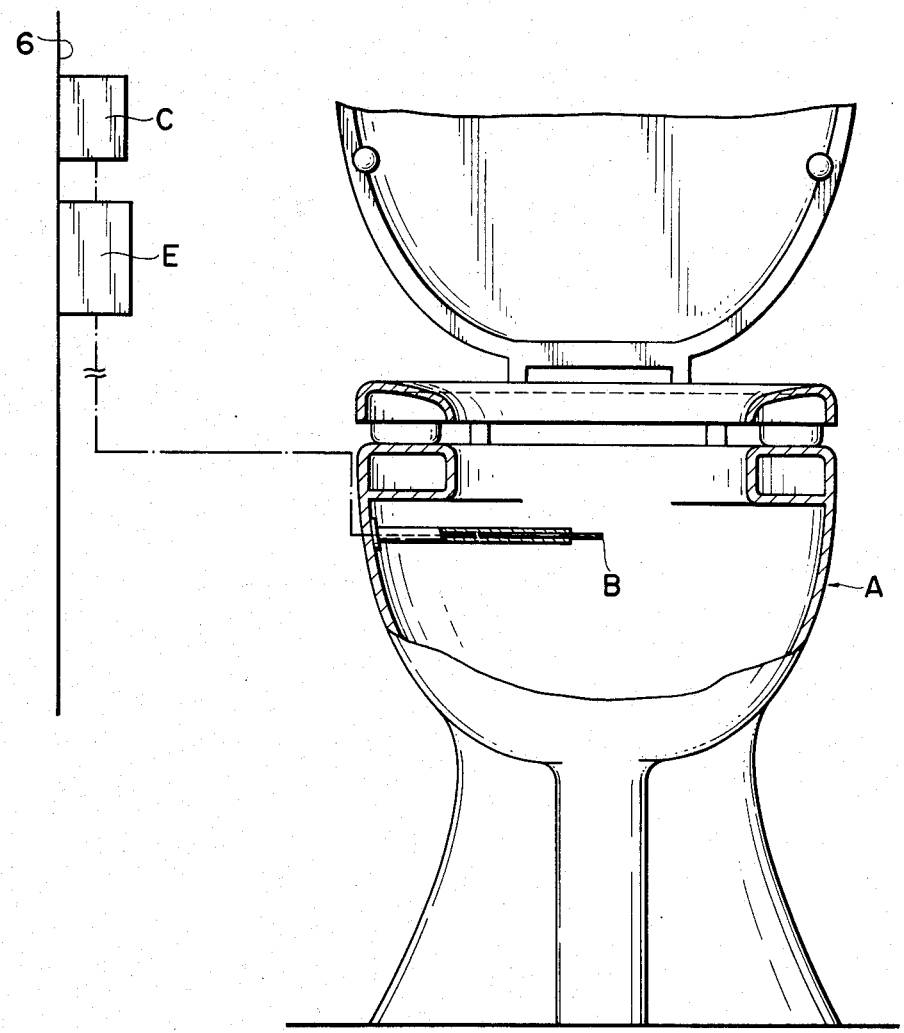
FIG. 9 is a front partial sectional view of a toilet apparatus in accordance with the present invention in which a detecting device for detecting the presence of a user is electrically connected to a sensor and to an indicator.
Figure 10:
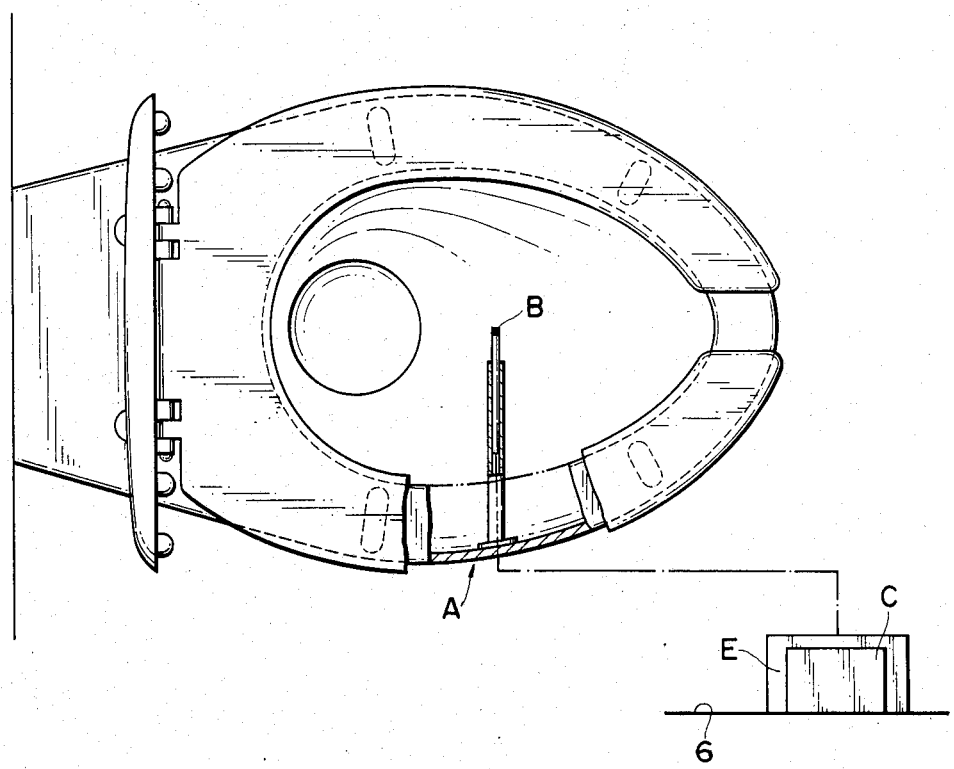
FIG. 10 is a top partial sectional view of the toilet apparatus illustrated in FIG. 9.

Detecting device E, as shown in FIGS. 9 and 10, can consist of a circuit for receiving reflected light, a delay circuit, a connection circuit for activating Sensor B which projects into bowl (a), the connecting circuit also serving to activate indicator C; the detecting device further comprises a single shot circuit for activating an electromagnetic flash bulb in order that the stool can be automatically flushed. Alternately, detecting device E need not include a single shot circuit, and the stool can be flushed manually in normal fashion.

We claim:

1. A toilet apparatus comprising a detecting sensor for detecting constituents contained in the excrements of a user of said toilet apparatus, an arm to which said sensor is connected, operating means for turning said arm with respect to a toilet bowl within which said apparatus is adapted to be positioned, said arm being connected to a rotary solenoid positioned below the seat of said toilet bowl, a mechanical switch comprising means for activating said solenoid and means for turning said arm into said toilet bowl to contact said sensor with said excrement, and an indicator which is electrically connected to said sensor, said indicator comprising means for analyzing and evaluating the health of said toilet user in response to the constituents which are detected in the excrements by said sensor.

2. A toilet apparatus in accordance with claim 1 wherein said detecting sensor is selected from a group of a biosensors, said group comprising enzyme sensors, organella sensors, tissue sensors, microorganism sensors, immunity sensors, enzyme thermistors, and light emitting immunity sensors.

3. A toilet apparatus in accordance with claim 1 wherein said detecting sensor comprises a BOD sensor or an electrochemical sensor.

4. A toilet apparatus in accordance with claim 1, said indicator comprising a central processing unit adapted to retain data corresponding to the values of the constituents of the excrements a healthy human being.

5. A toilet apparatus in accordance with claim 4 wherein said indicator comprises means for analyzing and evaluating the health of a toilet user in response to the constituents detected the excrements of said user.

6. A toilet apparatus in accordance with claim 5 wherein said indicator means indicates said analyzed results by emitting a descriminating sound.

7. A toilet apparatus in accordance with claim 5 wherein said indicating means comprises means for emitting a blinking light.

8. A toilet apparatus comprising means for detecting constituents in the excrements of a user and means for activating said detecting means, said detecting means comprising a detecting sensor and said activating means comprising means for activating said detecting sensor in response to detection of the presence of a user seated on said toilet apparatus.

9. A toilet apparatus in accordance with claim 8, said detecting sensor comprising a biosensor.

10. A toilet apparatus in accordance with claim 9, wherein said biosensor is selected from the group comprising enzyme sensors, organella sensors, tissue sensors, microorganism sensors, immunity sensors, enzyme thermistors, and light emitting immunity sensors.

11. A toilet apparatus in accordance with claim 9, wherein said detecting sensor is selected from the group consisting of BOD sensors and electrochemical sensors.

12. A toilet apparatus comprising means for detecting constituents in the excrements of a user and means for activating said detecting means, said detecting means comprising a detecting sensor, wherein said means for activating said sensor comprises an electrically conductive light receiving circuit having an infrared radiation emitting element and a receiving element for receiving light radiation reflected by a user from said infrared radiation emitting element.

13. A toilet apparatus in accordance with claim 12, wherein said activating means further comprises an amplifier circuit adapted to be activated when said radiation receiving circuit receives light.

14. A toilet apparatus in accordance with claim 13, wherein said activating means further comprises a delay circuit for retarding activation of said detecting sensor for a period of approximately 3-7 seconds.

15. A toilet apparatus in accordance with claim 14 wherein said delay circuit comprises means for preventing activation of said detecting sensor by passersby.

16. A toilet apparatus in accordance with claim 15 further comprising means for pivotally moving said detecting sensor from a position in which it is located below the seat of said toilet into a position in which it is angled downwardly a bowl, said pivoting means comprising a rotary solenoid adapted to activate said indicating means.

17. A toilet apparatus in accordance with claim 16 further comprising a strain gauge for repositioning said sensor into a position in which it is located below said stool seat by said solenoid after said sensor has contacted the excrement of a user.

18. A toilet apparatus in accordance with claim 8 further comprising means for indicating the constituents detected by said sensor, and a central processing unit adapted to receive prerecorded values corresponding to the constituents of the excrements of a healthy individual.

19. A toilet apparatus in accordance with claim 18 wherein said toilet apparatus further comprises means for analyzing the health of the user by comparing the value of the constituents detected by said sensor with said prerecorded values, said indicating means adapted to display an analyzed value indicating said user's health.

20. A toilet apparatus in accordance with claim 19 wherein said indicating means comprises means for emitting a sound corresponding to said detected constituents.

21. A toilet apparatus in accordance with claim 19 wherein said indicating means displays said analyzed result by emitting a blinking light.

22. A toilet apparatus in accordance with claim 21 wherein said blinking light is colored.

23. A toilet apparatus comprising a detecting sensor for detecting constituents contained in excrements of a user of said apparatus, an arm on which said sensor is positioned, operating means for turning said arm with respect to a toilet bowl within which said toilet apparatus is adapted to be positioned, said arm being connected to a rotary solenoid positioned below the seat of said toilet, means for activating said detecting sensor, said activating means being connected to said operating means, and an indicator which is electrically connected to said sensor, said indicator comprising means for analyzing and evaluating the health of the toilet user in response to the constituents detected in said excrements, wherein said sensor activating means comprises an electrically conductive light receiving circuit having an infrared radiation emitting element and a receiving element for receiving light radiation reflected by a user from said infrared radiation emitting element, an amplifier circuit adapted to be activated when said radiation receiving element receives light, and a delay circuit for retarding activation of said detecting sensor for a predetermined period.

24. A toilet apparatus in accordance with claim 23 wherein said delay circuit comprises means for preventing activation of said detecting sensor by a passerby for approximately 3-7 seconds.

25. A toilet apparatus in accordance with claim 24 further comprising a strain gauge for repositioning said sensor into a position in which it is located below said toilet seat by said solenoid after said sensor has contacted the excrement of the user.

26. A toilet apparatus in accordance with claim 24 wherein said biosensor is selected from the group comprising enzyme sensors, organella sensors, tissue sensors, microorganism sensors, immunity sensors, enzyme thermistors, and light emitting immunity sensors.

27. A toilet apparatus in accordance with claim 24, wherein said detecting sensor is selected from the group consisting of BOD sensors and electrochemical sensors.

28. A toilet apparatus in accordance with claim 24, wherein said indicator comprises a central processing unit adapted to receive prerecorded values corresponding to the constituents of the excrements of a healthy individual.

29. A toilet apparatus in accordance with claim 28 further comprising means for analyzing the health of a user by comparing the value of the constituents detected by said sensor with said prerecorded values, said indicator comprising means for displaying an analyzed value indicating the health of said user.

30. A toilet apparatus in accordance with claim 29 wherein said indicator comprises means for emitting a sound corresponding to said detected constituents.

31. A toilet apparatus in accordance with claim 29 wherein said indicator comprises means for displaying said analyzed value by emitting a blinking light.

32. A toilet apparatus in accordance with claim 31 wherein said blinking light is a colored light.

* * * * *